United States Patent [19]

Letourneur

[11] Patent Number: 5,017,384

[45] Date of Patent: May 21, 1991

[54] MEDICINAL COMPOSITION FOR REGULARIZING HORMONAL SECRETION AND FOR TREATING STERILITY

[76] Inventor: Bernard Letourneur, Le Champ du Bourray, Route de Oizé, Guecelard, Arnage, France, 72230

[21] Appl. No.: 388,632

[22] Filed: Aug. 2, 1989

[30] Foreign Application Priority Data

Aug. 2, 1988 [FR] France .................. 88 10432

[51] Int. Cl.$^5$ ............... A61K 33/42; A61K 33/14; A61K 33/04
[52] U.S. Cl. ........................ 424/601; 424/663; 424/705
[58] Field of Search .............. 424/601, 663, 705

[56] References Cited

U.S. PATENT DOCUMENTS

| | | | |
|---|---|---|---|
| 4,119,089 | 10/1978 | Preti et al. | 436/120 |
| 4,383,035 | 5/1983 | Sugimoto | 935/71 |
| 4,774,089 | 9/1988 | Ashmead | 514/492 |

OTHER PUBLICATIONS

Vidal, Louis, "Dictionnaire Vidal", Feb. 3, 1961, p. 1014: Magsalyl, Office de Vulgarisation Pharmaceutique, Paris, France.
Chem. Abst., 109:148295q (1988), Barhoum et al.

Primary Examiner—Stanley J. Friedman
Assistant Examiner—Zohreh A. Fay
Attorney, Agent, or Firm—Fleit, Jacobson, Cohn, Price, Holman & Stern

[57] ABSTRACT

A medicinal composition for regularizing hormonal secretion and for treating sterility comprises (a) sulfur, (b) calcium chloride and (c) phosphorus pentoxide, the weight ratio a:b being between 1:0.5 and 1:2 and the weight ratio (a+b):c being between 3.6 and 4.5. The composition is preferably for oral administration. It regularizes hormonal secretion in humans and animals, particularly in the treatment of sterility of women and female animals.

8 Claims, No Drawings

MEDICINAL COMPOSITION FOR REGULARIZING HORMONAL SECRETION AND FOR TREATING STERILITY

BACKGROUND OF THE INVENTION

The invention concerns a medicinal composition for regularizing hormonal secretion in men and women and for treating sterility in women and female animals.

This medicinal composition combats feminine sterility by regularizing periods, oestrogen secretion (folliculine or oestrogen), progesterone secretion and prolactine levels.

A medicinal composition according to the invention also helps to regularize secretion of TSH (thyreostimuline) by hypophysis, thereby combatting hypothyroidism, in particular lack of $T_3$ (triiodothrionine), $T_4$ (thyroxine) and $FT_4$ (free $T_4$).

This medicinal composition is also active in the synthesis and secretion of hypophyseal FSH (follicle stimulating hormone) and in synthesis of LH (luteinizating hormone).

Regularizing FSH levels enables LH to act on the ovaries.

An object of the invention is to provide a medicinal composition for regularizing hormonal secretion and for treating female sterility.

Another object of the invention is to provide a medicinal composition for reducing prolactine levels, particularly by the action of calcium chloride.

A further object of the invention is to provide a medicinal composition for treating hypothyroidism.

A still further object of the invention is to provide a medicinal composition for regularizing periods and encouraging ovulation in women and female animals.

SUMMARY OF THE INVENTION

A medicinal composition according to the invention comprises as active elements:

(a) sulfur,
(b) calcium chloride $CaCl_2$, and
(c) phosphorus pentoxide $P_2O_5$.

The sulfur is preferably in the form of flowers of sulfur.

The weight ratio a:b lies between 1:0.5 and 1:2, advantageously between 1:1.5 and 1:1.7.

The weight ratio (a+b):c lies between 4.5 and 3.6, advantageously between 4.1 and 4.5.

An advantageous weight ratio of a:b:c is 1.6:0.6.

In a preferred embodiment the medicinal composition is administered orally.

The medicinal composition may also be administered rectally.

When administered orally, the medicinal composition may contain an excipient or vehicle preferably in powder form, or it may contain no excipient and be in capsule form.

When it contains excipients the medicinal composition may be packaged as pills, compressed tablets or sugar coated tablets or in any other appropriate form.

The medicinal composition may of course comprise any other excipient or vehicle routinely used in the preparation of medication.

In particular the following may be used:
vehicles such as starches, sugars, mannitol or lactose;
binding agents such as carboxycellulose, carboxymethylcellulose and other cellulose derivatives, alginates, gelatine or polyvinylpyrrolidine;
wetting agents such as glycerine;
lubricants such as talc;
perfumes and taste enhancers.

Particularly advantageous galenic forms for oral administration include capsules, compressed tablets and sugar coated tablets but any galenic form suitable for oral administration may be employed.

In suppositories for rectal administration, excipients such as cocoa butter, hydrogenated oils, hydrogenated and polyoxyethylenated oils, solid semisynthetic glycerides, polyoxyethyleneglycols and other excipients generally used in the manufacture of suppositories may be used.

The recommended daily dose is between 2.5 and 3.8 g of a medicinal composition comprising:
0.8 to 1.2 g sulfur,
1.3 to 1.9 g calcium chloride, and
0.5 to 0.7 g phosphorus pentoxide.

Advantageously, a daily dose is 3.2 g of a medicinal composition comprising:
1.0 g sulfur,
1.6 g calcium chloride,
0.6 g phosphorus pentoxide.

The recommended posology consists in administering the above dose in two halves as a capsule or tablet at midday and another capsule or tablet in the evening, each to be taken with a meal.

To treat feminine sterility, administration is commenced on the 24th day after the preceding period and continued during the period.

The effects of the composition are monitored by measuring the patient's levels of oestradiol, progesterone and the hormones LH and FSH.

It is preferable not to take during the treatment medication containing antibiotics, antiinflammation agents and antipyretic antalgics such as paracetamol and aspirin which may have an unfavorable influence on the action of the inventive medicament.

It is also important not to use tampons during treatment.

The medicinal composition according to the invention has been tested on animals as well as on men and women volunteers.

The following examples illustrate the invention:

EXAMPLES OF THE INVENTION

EXAMPLE 1

The following analysis results were obtained for woman volunteer No. 1 before treatment and after eight weeks' of treatment:

|  | Before treatment: analysis 24 days after period | After one month's treatment: analysis 24 days after period | Adult norm for luteal phase |
| --- | --- | --- | --- |
| plasmic oestradiol | 24.8 ng/l | 104 ng/l | 70 to 250 ng/l |
| plasmic progesterone | 0.4 μg/l | 13.4 μg/l | 4.7 to 20 μg/l |
| plasmic LH | 9.4 IU/l | 2.1 IU/l | 1 to 9 IU/l |
| plasmic FSH |  | 4 IU/l | 1.5 to 12 IU/l |

It can be seen that the treatment raised the oestradiol and progesterone levels, reduced the level of plasmic LH and regularized the level of plasmic FSH.

EXAMPLE 2

The following analysis results were obtained for woman volunteer No. 2 on the 24th day following the start of a period and before treatment:

| oestradiol: | 0.1 ng/ml |
|---|---|
| plasmic LH: | 24.72 mIU/ml |
| plasmic FSH: | 4.80 mIU/ml |
| prolactine: | 4.41 ng/ml |

A very low oestradiol level and a very high plasmic LH level were observed.

After two months' treatment the oestradiol level had increased to 240 ng/ml

EXAMPLE 3

The following results were obtained for woman volunteer No. 3 on the 24th day following the start of a period and before treatment:

| oestradiol: | 0.5 ng/ml |
|---|---|
| progesterone: | less than 0.1 µg/l |
| plasmic LH: | 13.50 IU/l |
| plasmic FSH: | 4.0 IU/l |

After six weeks' treatment and on the 24th day after a period the oestradiol level had increased to 250 ng/ml and the progesterone level had increased to 16 µg/l.

The treatment had regularized the hormone levels in all three cases and all three volunteers became pregnant.

There is claimed:

1. A medicinal composition for regularizing hormonal secretion and for treating sterility in women and female animals, comprising effective amounts of the elements sulfur, calcium chloride and phosphorous pentoxide, wherein said effective amounts are effective for regularizing hormonal secretion and for treating sterility when provided in the composition.

2. The medicinal composition of claim 1, wherein the weight ratio of sulfur to calcium chloride is between 1:0.5 and 1:2 and the weight ratio of the total weight of sulfur and calcium chloride: to phosphorous pentoxide is between 4.5 and 3.6.

3. The medicinal composition of claim 1, wherein the weight ratio a:b:c of sulfur to calcium chloride to phosphorous pentoxide is 1:1.6:0.6

4. The medicinal composition of claim 8, wherein said excipient is a solid and said composition is in the form of a compressed tablet, pill or in any other suitable solid form.

5. The medicinal composition of claim 1, further comprising an additive selected from the group consisting of vehicles, binding agents, wetting agents, lubricants, perfumes and taste enhancers.

6. The medicinal composition of claim 1 in capsule form.

7. The medicinal composition of claim 1 in the form of a suppository.

8. The composition of claim 1, further comprising an excipient.

* * * * *